United States Patent
Hansen

(10) Patent No.: US 6,595,041 B2
(45) Date of Patent: Jul. 22, 2003

(54) METHOD AND APPARATUS FOR MAGNETIC LEVITATION

(75) Inventor: Brian Nils Hansen, 401 Mountain View Ave., Longmont, CO (US) 80501

(73) Assignee: Brian Nils Hansen, Longmont, CO (US)

(*) Notice: Subject to any disclaimer, the term of this patent is extended or adjusted under 35 U.S.C. 154(b) by 0 days.

(21) Appl. No.: 09/892,437

(22) Filed: Jun. 28, 2001

(65) Prior Publication Data

US 2002/0124765 A1 Sep. 12, 2002

Related U.S. Application Data

(60) Provisional application No. 60/214,359, filed on Jun. 28, 2000.

(51) Int. Cl.⁷ .................. G08B 21/00; G01F 1/28; F16C 32/04; B66B 7/02; H02N 15/00
(52) U.S. Cl. .................. 73/53.01; 73/54.01; 73/514.31; 73/862.626; 73/DIG. 3; 324/207.2; 324/204
(58) Field of Search .................. 73/53.01, 54.01, 73/54.04, 514.31, DIG. 3, 862.626, 1.79, 570.5; 324/207.2, 207.21, 204

(56) References Cited

U.S. PATENT DOCUMENTS

| | | | | |
|---|---|---|---|---|
| 4,191,951 A | * | 3/1980 | Fuzzell | 340/610 |
| 4,619,146 A | * | 10/1986 | Teodorescu et al. | 73/861.54 |
| 4,698,562 A | * | 10/1987 | Gale et al. | 318/254 |
| 5,168,183 A | * | 12/1992 | Whitehead | 310/12 |
| 5,294,757 A | * | 3/1994 | Skalski et al. | 187/115 |
| 5,308,938 A | * | 5/1994 | Roberts et al. | 187/115 |
| 5,321,217 A | * | 6/1994 | Traktovenko et al. | 187/115 |
| 5,359,490 A | * | 10/1994 | Oguro | 361/144 |
| 5,379,864 A | * | 1/1995 | Colby | 187/393 |
| 5,491,633 A | * | 2/1996 | Henry et al. | 364/424.05 |
| 5,980,193 A | * | 11/1999 | Clifton et al. | 414/749 |
| 6,035,703 A | * | 3/2000 | Abnett | 73/54.01 |
| 6,353,273 B1 | * | 3/2002 | Heshmat et al. | 310/90.5 |

* cited by examiner

*Primary Examiner*—Helen Kwok
*Assistant Examiner*—David J. Wiggins

(57) ABSTRACT

A method to maintain magnetic levitation that is stabilized by means of Hall effect sensors is disclosed. The method and device comprising a Hall effect sensor or sensors used to control an electromagnet to maintain the position between two magnets or objects. The present invention has been used to suspend a magnet in a high pressure tube that is magnetically coupled to a magnet outside the tube connected to an analytical balance that can accurately measure the force on the magnet inside the tube. This force measurement can be used to determine fluid density, flow, viscosity, and solubility. This magnetic levitation method also has application for other devices such as motors, generators, trains, turbines, wind tunnels, and entertainment devices.

10 Claims, 2 Drawing Sheets

METHOD AND APPARATUS FOR MAGNETIC LEVITATION

This application claims the benefit of Provisional application Ser. No. 60/214,359, filed Jun. 28, 2000.

FIELD OF THE INVENTION

The present invention relates to methods and apparatus for magnetic levitation or suspension of an object, part or magnet at a desired position that is electronically stabilized with Hall effect sensors.

BACKGROUND OF THE INVENTION

There are many applications for utilizing magnetic levitation to minimize friction, make force measurement, design, and entertaining devices. Friction can be minimized by magnetic levitation for motors, turbines, generators, trains, projectile guns, etc. Magnetic suspension or levitation is an important technique to measure force on an object in a wind tunnel. Wires, cables etc. used to suspend an object in a wind tunnel will interfere with the force measurement. Some fluid density measurements require magnetic suspension to prevent surface tension from interfering with buoy suspension line. High pressure fluid density measurement require magnetic suspension to measure the force on a buoy through the walls of a high pressure vessel. A number of magnetic levitation devices have been built to demonstrate a floating object with no visible support, which spectacular feature is commonly known to the general public via the manufacture of various novelty or entertainment devices.

There are many applications for magnetic levitation that require position sensing and feedback control. Stable magnetic levitation or suspension can be achieved in a totally passive system using a superconductor. However, in some cases it is not possible or practical to use a passive system. Magnetic levitation can be accomplished in an active system using an electromagnet, position sensor, and feedback control circuit. The electromagnet is driven with an electrical current which is used to maintain the levitated object in a stable position at a general location situated beneath the electromagnet. The position sensor detects the position of the levitated object for the feedback circuit. The feedback circuit controls the current in the electromagnet to maintain a given position. Stable magnetic levitation is maintained in the system by increasing the lifting current in the electromagnet when the object falls away from the electromagnet and the lifting current decreases when the levitated object moves up towards the electromagnet. A number of different position sensors are currently used to maintain stable magnetic levitation. The position of a levitated object can be detected optically when a light beam is interrupted and the optical detector changes the current in the lifting coil. In the case of measuring fluid properties or fluid conditions, this limits fluid measurement to optically transparent fluids and vessels, where the range of possible fluid measurements include, but are not limited to, flowrate, density, viscosity, phase change, and phase equilibria properties. A liquid meniscus or droplet can also interfere with the light beam. Inductive and capacitive detectors are also limited by the materials that the fluid containment vessel is made of. Hall effect sensors can detect the position of a permanent magnet in tubes made of metals, ceramics, glass, sapphire, and any material that will allow some detectable magnetic field to penetrate the material. With the recent development of low cost amplified hall effect sensors and power amplifiers this technology is easily adapted to a wide variety of applications.

SUMMARY OF THE INVENTION

Accordingly, it is an object of the present invention to provide methods and apparatus for achieving electronically stabilized magnetic suspension of objects, parts or magnets at desired positions using hall effect sensors. It is a further objective of the present invention to provide methods and apparatus for, but not limited to, fluid property measurement, wind tunnel measurements, trains, monorails, transportation equipment, toys, novelty or entertainment devices etc.

BRIEF DESCRIPTION OF THE DRAWINGS

The following detailed description will be more fully understood in view of the drawing in which.

DETAILED DESCRIPTION

In accordance with the present methods for maintaining stable magnetic levitation, a hall effect sensor or hall effect sensors measure the position of a permanent magnet. The hall effect sensors control the current in an electromagnet to maintain the desired position between two permanent magnets. The present invention also relates to apparatus particularly adapted for use in connection with the described methods of magnetic levitation.

Figure 1:
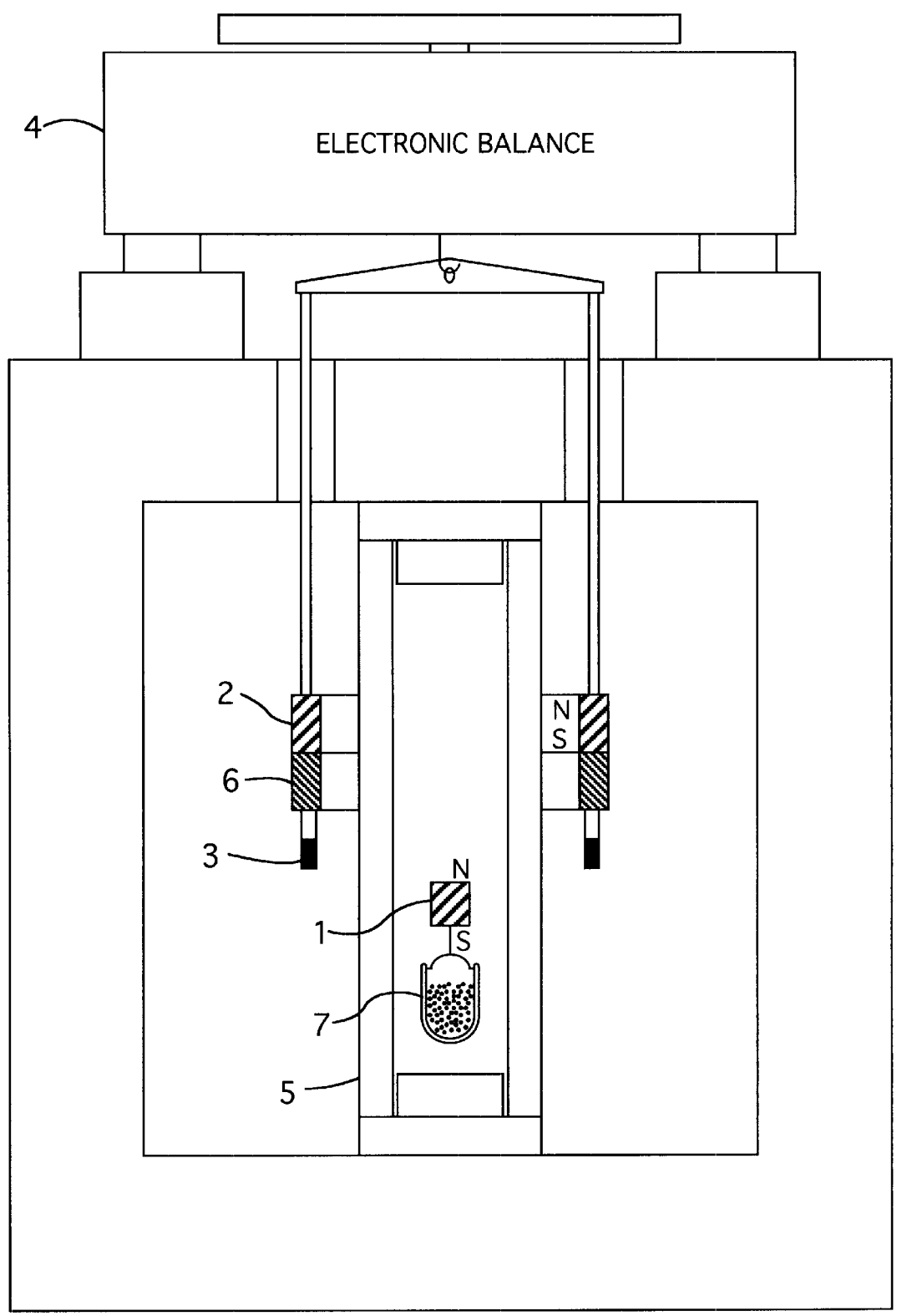
FIG. 1 sets forth a first embodiment of the apparatus according to the present invention.

An example of such an apparatus according to the invention is set forth in FIG. 1. With reference to FIG. 1, the cylindrical permanent magnet 1 is attracted to the ring permanent magnet 2. The hall effect sensors 3 detect the distance between the permanent magnets to maintain the desired distance with the current in the electromagnet 6. The electronic balance 4 measures the lifting force required for the cylindrical permanent magnet 1 suspended in the sapphire tube 5. The suspended holder 7 can be used to hold a solute for solubility measurement. Solubility measurement is performed when the solute dissolves in the solvent contained in the sapphire tube and the electronic balance measures the change in force.

Figure 2:
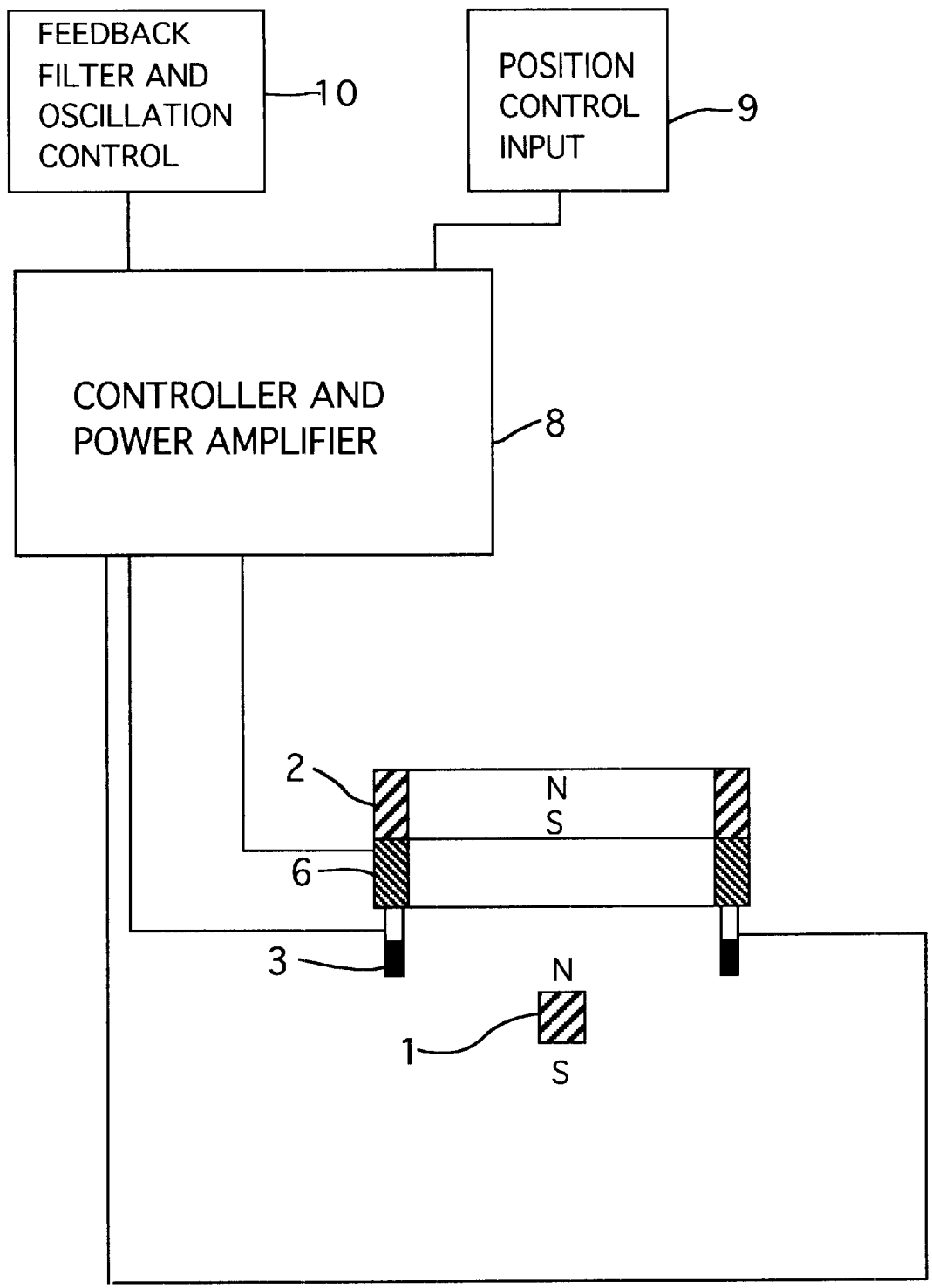
FIG. 2 sets forth an embodiment of the electronic control circuit of the apparatus set forth in FIG. 1.

The circuit shown in FIG. 2 can be used to control the position between the permanent magnets in FIG. 1. With reference to FIG. 2, the hall effect sensors 3 provide position information to the amplifier circuit 8 which controls the electrical current in the electromagnet 6. The position control circuit 9 can be used to change the position between the magnets, maintain a position that provides electromagnet coil current that is near zero, or cause the magnets to oscillate, etc. The circuit in 10 can be used to filter out oscillations and maintain high degree of stability, or measure lifting force for a given position.

EXAMPLE

The magnetic levitation system shown in FIG. 1 was used to measure the density of freon R-116(hexafluoroethane) at ambient temperature in a high pressure environment that ranges from 600 PSI to 1000 PSI. The solubility and saturated density for the binary system of R-116 and Iron Hexafluoroacetylacetonate was also measured in this pressure range.

What is claimed:

1. A method achieving an active system for magnetic levitation or suspension of a suspended object, part or magnet, comprising: an electromagnet for levitating or suspending said object, part or magnet at a known desired or maintained position, which electromagnet is controlled by two or more hall effect sensors wherein the two or more hall effect sensors are used to reduce or cancel signals resultant from any lateral movement of said suspended object, part or magnet, thereby providing better vertical control of said position of said suspended object, part or magnet.

2. A method achieving an active system for magnetic levitation or suspension of a suspended object, part or magnet, comprising: an electromagnet that is controlled by one or more hall effect sensors wherein levitation system is used to maintain the position between two permanent magnets that are oriented to have an attractive force.

3. The method of claim 2 wherein the electromagnet maintains a position between a ring shaped permanent magnet and solid permanent magnet.

4. The method of claim 2 further comprising the use, of an electronic amplifier or amplifiers to amplify the signal from the hall effect sensor to control an electromagnet or electromagnets.

5. The method of claim 4 wherein the electromagnets maintain a position between the permanent magnets such that the current in the electromagnet approaches zero.

6. The method of claim 4 wherein the signal from the hall effect sensor and the amplifier is used to change the position between said two permanent magnets.

7. The method of claim 4 wherein the magnetic suspension is used to measure the force on a suspended object.

8. The method of claim 4 wherein the magnetic suspension is used in reducing friction by means of non-contact bearings in mechanical machine and machinery applications consisting of motors, generators, trains, turbines and vacuum pumps.

9. A method that uses magnetic levitation or suspension to measure properties of a fluid including, but not limited to, flow rate, density, viscosity, and phase equilibria of a static or mobile fluid that is either contained in or flowing thru a tube further comprising an electromagnet or electromagnets controlled by two or more hall effect sensors, using an amplifier or amplifiers to amplify the signal from said sensors, further utilizing a ring shaped permanent magnet and electromagnet connected to a force measurement device or balance to measure the force on a permanent magnet suspended in said tube.

10. A method that uses magnetic levitation or suspension to measure the forces on an object suspended in a wind tunnel comprising an electromagnet(s) controlled by two or more hall effect sensors, further comprising the use of an amplifier(s) to amplify the signal from said hall effect sensors and power the electromagnet(s).

* * * * *